(12) United States Patent
Laermer et al.

(10) Patent No.: US 8,506,530 B2
(45) Date of Patent: Aug. 13, 2013

(54) MICRONEEDLES TO BE PLACED IN THE SKIN FOR THE TRANSDERMAL APPLICATION OF PHARMACEUTICALS

(75) Inventors: Franz Laermer, Weil Der Stadt (DE); Michael Stumber, Korntal-Muenchingen (DE); Dick Scholten, Stuttgart (DE); Christian Maeurer, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 1032 days.

(21) Appl. No.: 11/897,299

(22) Filed: Aug. 29, 2007

(65) Prior Publication Data
US 2008/0167601 A1 Jul. 10, 2008

(30) Foreign Application Priority Data
Aug. 30, 2006 (DE) .......................... 10 2006 040 642

(51) Int. Cl.
*A61M 5/00* (2006.01)
(52) U.S. Cl.
USPC ................. 604/173; 604/22; 604/46; 604/47; 604/191; 604/272; 604/273; 604/274; 604/506

(58) Field of Classification Search
USPC ............... 604/46, 173, 191, 22, 47, 272–274, 604/506
See application file for complete search history.

(56) References Cited

U.S. PATENT DOCUMENTS

| 2002/0082543 | A1 | 6/2002 | Park et al. |
| 2002/0138049 | A1 | 9/2002 | Allen et al. |
| 2003/0045837 | A1* | 3/2003 | Delmore et al. ............. 604/173 |
| 2003/0135167 | A1 | 7/2003 | Gonnelli |
| 2005/0118388 | A1* | 6/2005 | Kingsford ...................... 428/99 |
| 2005/0137531 | A1* | 6/2005 | Prausnitz et al. ............. 604/173 |
| 2006/0030812 | A1* | 2/2006 | Golubovic-Liakopoulos et al. ................................ 604/46 |

FOREIGN PATENT DOCUMENTS
WO  WO 02/062202  8/2002

* cited by examiner

*Primary Examiner* — Bhisma Mehta
*Assistant Examiner* — Larry R Wilson
(74) *Attorney, Agent, or Firm* — Kenyon & Kenyon LLP

(57) ABSTRACT

An array for placement on the skin of a human or animal patient for the purpose of the transdermal application of pharmaceuticals, toxins or active agents, having microneedles that are situated on a carrier substrate, the microneedles having a preset breaking point in the area of the transition to the carrier substrate.

16 Claims, 4 Drawing Sheets

MICRONEEDLES TO BE PLACED IN THE SKIN FOR THE TRANSDERMAL APPLICATION OF PHARMACEUTICALS

FIELD OF THE INVENTION

The present invention relates to micro-needles to be placed in the skin for the transdermal application of pharmaceuticals.

BACKGROUND INFORMATION

Experiments have been undertaken for a long time on administering pharmaceuticals and other active agents in sufficient doses by transdermal application. In many cases this would save patients an injection that is often annoying, painful and connected with the risk of infection, and, on the other hand, it could avoid oral application that is often annoying, difficult to control and almost impossible in the case of some medications.

Transdermal application has a series of advantages, especially in the case of children who are afraid of injections, and who are reluctant to take medications orally because of their bad taste, in the case of the chronically ill and in the case of geriatric patients.

Without additional measures, in the case of most substances, only a very small quantity of active agent can be absorbed through the skin per unit of time. The reason is that the skin represents, by its nature, a very effective permeation barrier for protecting the body from infections and environmental toxins.

For this reason, active agents that are to be administered through the skin have to be applied to the skin in large doses. As a rule, above all, those active agents are suitable for transdermal application which are to develop their action in close proximity to the place of application, in order to treat, for instance, inflammations or allergic reactions.

Only in a few cases can active agents, applied in that manner, get into the blood circulation in sufficient quantity, and develop a systemic effect. This approach is reserved for active agents which are able comparatively easily to penetrate the skin because of their size and their molecular character, or which have to be administered in extremely small doses.

Lipophilic substances, as a rule, are easily able to penetrate the upper skin layer (the stratum corneum). However, they are subsequently taken up into the blood only with difficulty, since doing this, in turn, requires hydrophilic properties. Therefore, in the case of direct transdermal application, it is necessary to formulate the substances in such a way that they are both sufficiently lipophilic and hydrophilic. Examples of substances successfully applicable via the skin are sex hormones, nicotine and scopolamine.

To improve the transdermal passage of the active agents, there are several approaches to reducing the barrier function of the skin for a time period of greater or lesser length. This may involve laserporation, ultrasound, iontophoresis, electroporation, liquid jets, powder jets or chemical supports. All approaches have their individual disadvantages and limitations. The first named are not established, so that, up to now, only the chemical supports (e.g. dimethylsulfoxide) are used to a greater extent.

A different approach falling under this category is the use of microneedles, with whose help the stratum corneum of the skin is penetrated. The microneedles are frequently situated in the form of arrays. The needles are subsequently removed, a plaster containing active agents is applied externally, and the active agents released by it are then able to pass through the skin more easily.

In this manner, a diffusion rate through the skin of the active agents, that is increased by several orders of magnitude ($10^3$-$10^9$), is achieved, and new active agents for transdermal application can be developed.

Microneedle arrays for this purpose are discussed, for example, in U.S. Pat. No. 6,334,856.

However, this approach also has a series of disadvantages. For instance, the taking up of the active agent by the microinjuries brought about is poorly defined, since the size of the permeations generated and the complete healing rate, and thus the rate of reclosure, are individually different. Thus, the administered dose is hard to determine. Moreover, the microinjuries that are generated make possible the passage through the skin of infective agents. Consequently, the method involves a considerable risk of infection.

Microneedle arrays are known in the related art which remain in the skin during the application of the medication. The microneedles have a porous structure and/or a central channel in order to be passable to the pharmaceuticals, toxins or active agents applied from the outside. Such arrays are discussed, for example, in U.S. Pat. No. 6,908,453, and in U.S. Published Patent Applications Nos. 2006/030812 and 2005/261632.

Beyond this, U.S. Pat. No. 7,770,480 explains that the microneedles can be produced from microporous silicon which, on the one hand, makes possible the passage of the active agents and, on the other hand, has biocompatible properties.

It is a disadvantage of all the arrays that they have to be removed again after the therapy, open microinjuries being produced by this which make possible the passage of infective agents through the skin as well. Consequently, the method involves a considerable risk of infection. Besides, handling is made more complicated by the need to remove the array again. Furthermore, there is the danger that parts of the microneedles break off and remain in the body, and are rejected by the immune system if no material is used that is easily broken down by the body.

SUMMARY OF THE INVENTION

It is an object of the exemplary embodiments and/or exemplary methods of the present invention to make available a microneedle array for the transdermal application of pharmaceuticals which involves little danger of infection and makes simple handling possible.

This object may be attained using the features described herein, including as to the specific embodiments.

Accordingly, an array is provided to be placed on the skin of a human or animal patient for the purpose of the transdermal application of pharmaceuticals, toxins or active agents. The array has microneedles that are situated on a carrier substrate and have preset breaking points in the area of the transition to the carrier substrate.

This preset breaking point can be developed, for instance, in the form of a material tapering or a constriction at the foot of the needles. In this specific embodiment the needle array is placed into the skin using the carrier substrate. Thereafter, for instance with the aid of a lateral shearing motion or a vibrating motion of the carrier substrate, the latter is disengaged from the microneedles, the needles that have broken off remaining in the skin. The introduction of the active agents can be managed either through active agents already held in reserve in the porous needle material or through active agent preparations applied from the outside, via the needles.

In addition, the preset breaking points can contribute to placing the needles securely in the skin, since the skin is elastic and has the tendency to draw together around the needles more strongly in the region of the taperings.

It is prevented by this that, after the termination of the therapy, the array has to be removed as a whole, and that thereby large-surface microinjuries are laid open. Instead, during the therapy, only the microneedles remain in the skin. It may be provided, in this context, that these will dissolve after a predetermined time, so that they do not have to be actively removed (that is, by the doctor or the patient). We shall discuss this further below.

The microneedles may be designed in the form of cannulas. The microneedles may have a length of 20-800 μm, a diameter of 5-150 μm and a tip diameter of 0.5-20 μm. The microneedles may be arranged in rectangular or hexagonal alignment. However, a purely random arrangement of the microneedles may also be provided.

The array according to the exemplary embodiments and/or exemplary methods of the present invention may have a size of 1×1 mm to 30×30 mm. However, the array does not have to be square or rectangular; rather, it can also assume a surface that is circular, oval or of another shape. In addition, arrays bordered by straight lines have the disadvantage that the edges may cut into the skin, the carrier substrate may be planar.

In one particularly embodiment, the microneedles and/or the carrier substrate are made up of a material containing silicon.

The microneedles may have a partially or entirely porous structure. The porous structure is used, on the one hand, to make the microneedles permeable to the pharmaceuticals to be applied and/or to store them. Besides that, in the course of time the microneedles made of a porous silicon material dissolve in body fluids to form silicic acid (biodegradability, "biosilicon"), so that the needles, once in place, do not have to be removed again. The functional duration and the retention duration of the microneedles in the skin can be determined by the suitable selection of the parameters that determine the porosity.

Because the microneedles remain in the skin, the risk of infection is minimized on the one hand, and on the other hand a defined access is created for the active agent to pass through, so that more accurate dosing becomes possible.

The array according to the exemplary embodiments and/or exemplary methods of the present invention is particularly suitable for the application of hormones, including insulin and contraceptives, anticoagulants, antiemetics, analgesics, antidepressives, antipsychotics, anxiolytics, antiparkinson agents, antidiabetic agents, antiosteoporosis agents, antibiotics, vaccines, antiarrhythmic agents and vaccination substances.

The application of the pharmaceuticals, etc., can be accomplished in two different ways, in this instance. In a first embodiment it can be provided that the pharmaceuticals are already held in reserve in the porous needle material and are administered through the skin in a time-delayed manner. This embodiment is particularly suitable for active agents that are highly effective and given at low doses, such as vaccination substances or allergenics for the desensitization of allergic persons.

In a second embodiment it can be provided that the microneedles only represent a passageway for active agent preparations applied from the outside. In this connection, what may be involved is a gel applied from the outside, an ointment, a plaster containing active agents, a reservoir or the like. It may particularly be sufficient, in this instance, that the microneedles have a porous structure which can be passed through more easily by the active agents applied from the outside.

In an additional embodiment it is provided that the microneedles are developed in the form of cannulas. This means that they have a central channel. The diameter of this channel may be in the range of 2-20 μm. This type of embodiment is particularly suitable for those active agents that have to be administered in relatively high doses.

In a further embodiment it can be provided that the planar carrier substrate is developed in such a way that it is able to remain on the spot after the array is placed on the skin.

For this purpose it can particularly be provided that the carrier substrate is a flexible carrier substrate. In this embodiment, the array can be placed on the skin and the carrier substrate remains on the spot. During the course of treatment or after termination of the treatment, the carrier substrate can be removed again from the skin, microneedles that have possibly not yet been resorbed or dissolved being also removed.

A plaster-like substrate may particularly be involved as such a carrier substrate which, for one, has an adhesive layer with the aid of which the substrate is immobilized on the skin, and the penetration of germs and pathogens is prevented. In addition, the plaster-like substrate can function as storage for the active agent.

However, the carrier substrate can also take over only a purely physical carrier function, that is, the above-described additional tasks such as protection from infection and/or storage and the release of active agents, can also be taken over by additional materials that are specifically provided for the purpose, which are subsequently applied to the carrier substrate from the outside.

In one embodiment it is provided that the needles have a structure on their surface that functions as a barbed hook. This embodiment also contributes to placing the microneedles securely in the skin.

In addition, the exemplary embodiments and/or exemplary methods of the present invention provides a kit of parts made up of an array according to one of the preceding claims, as well as a cover material which can be placed over the array from the outside, after the array is placed in the skin.

Such a cover material may, for instance, be a plaster-like substrate. This may have an adhesive layer, on the one hand, with the aid of which the array is immobilized on the skin. Besides, the cover material is able to contribute to preventing the penetration of germs and pathogens and/or function as storage for active agents. For the latter, the cover material may have storage in the form of a cushion containing a silica gel matrix.

In this context, the cover material can be used in both the aforenamed embodiments, that is, both in the embodiment in which the carrier substrate is disengaged and removed from the needles, after the placing of the array in the skin, and in the embodiment in which the carrier substrate is developed to be flexible and can remain after the placement of the array on the skin.

In addition to that, a method is provided for producing an array according to the present invention. The method includes preparation of a substrate made of a material containing silicon; the application of an etching mask onto the substrate using a photolithographic method; and the etching of the desired structures using isotropic and anisotropic etching methods. What is involved here, for example, is a three-dimensional etching method as was proposed, for instance, by Laermer et al. (1999) "Bosch Deep Silicon Etching: Improving Uniformity and Etch Rate for Advanced MEMS Applications", Micro Electromechanical Systems, Orlando, USA.

Furthermore, according to the exemplary embodiments and/or exemplary methods of the present invention a method is provided for using microneedle arrays according to one of the preceding claims. The method has the following steps:
a) the application of a microneedle array onto the skin or the body surface, according to one of the preceding
b) the insertion of the needles of the microneedle array into the outer skin layers by the exertion of pressure
c) the separation of the microneedles from the carrier and the removal of the carrier
d) the administration of pharmaceuticals, toxins or active agents via the openings created using the microneedles.

These openings can remain for a time period between 1-2 hours and a few weeks. Since the microneedles dissolve over time, the removal of a microneedle after termination of the therapy is not required.

The separation of the microneedles may take place by a shearing motion. The separation of the microneedles from the carrier can likewise take place by a vibrational motion.

In one embodiment, the microneedles are surrounded by a thin film or a foil which is pierced when the microneedles are inserted into the skin and which lies down on the skin. This film may be a thin polyurethane film.

The exemplary embodiments and/or exemplary methods of the present invention is explained more accurately by the figures shown and discussed below. It should be noted, in this instance, that the figures have only a descriptive character and are not intended to restrict the present invention in any form. In particular, the microneedles do not have to be round, but may also assume angular shape having straight, concave or convex sidewalls.

DETAILED DESCRIPTION

Figure 1:
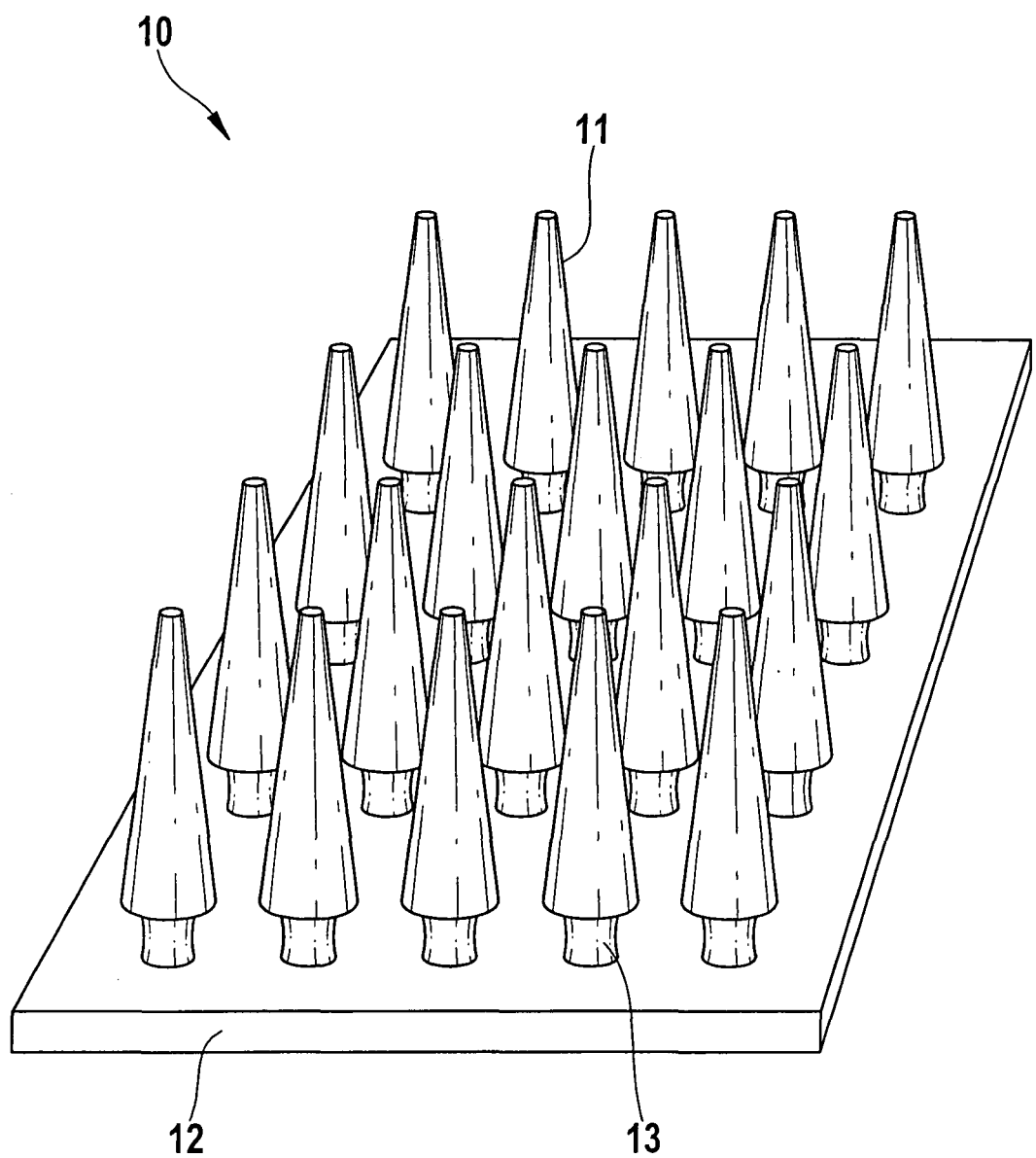
FIG. 1 shows an array 10 made of microneedles 11 according to the exemplary embodiments and/or exemplary methods of the present invention.

FIG. 1 shows an array 10 made of microneedles 11 according to the exemplary embodiments and/or exemplary methods of the present invention, in a rectangular arrangement with respect to one another, in a perspective view. The array is suitable to be placed on the skin of a human or animal patient for the purpose of the transdermal application of pharmaceuticals, toxins or active agents. Microneedles 11 are made up of a material containing silicon, and have a porous structure that is not shown in FIG. 1. The introduction of the active agents can be managed either through active agents already held in reserve in the porous needle material or through active agent preparations applied from the outside.

Figure 2A:
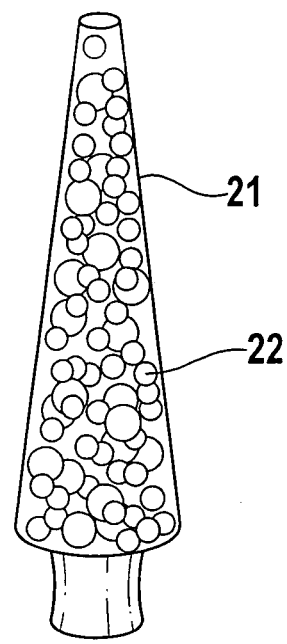
FIG. 2a shows a first embodiment of a microneedle 21 of an array according to the exemplary embodiments and/or exemplary methods of the present invention.

FIG. 2a shows a first embodiment of a microneedle 21 of an array according to the present invention. Microporous structure 22 is easy to recognize, which is used, on the one hand, to make the microneedles permeable to the pharmaceuticals to be applied from the outside, and to store these. Besides that, in the course of time, the microneedles made of a porous silicon material dissolve in body fluids to form silicic acid (biodegradability, "biosilicon"), so that the needles, once in place, do not have to be removed again. The retention duration of the microneedles in the skin can be determined by the suitable selection of the parameters that determine the porosity.

Figure 2B:
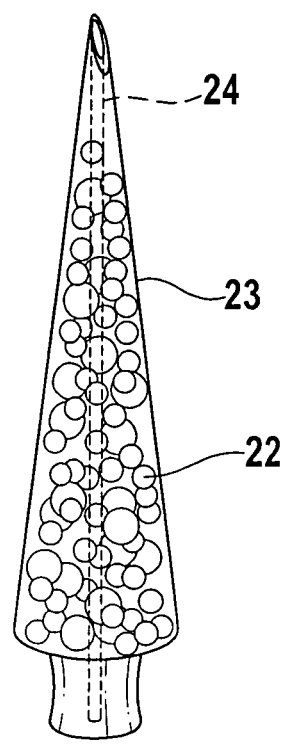
FIG. 2b shows a further embodiment of a microneedle 23 of an array according to the exemplary embodiments and/or exemplary methods of the present invention.

FIG. 2b shows a further embodiment of a microneedle 23 of an array according to the present invention, which has a centrical channel 24 besides microporous structure 22, and which thus forms a cannula. In this embodiment, the introduction of active agent may take place via channel 24, while the microporous structure is predominantly used for degradability.

Figure 2C:
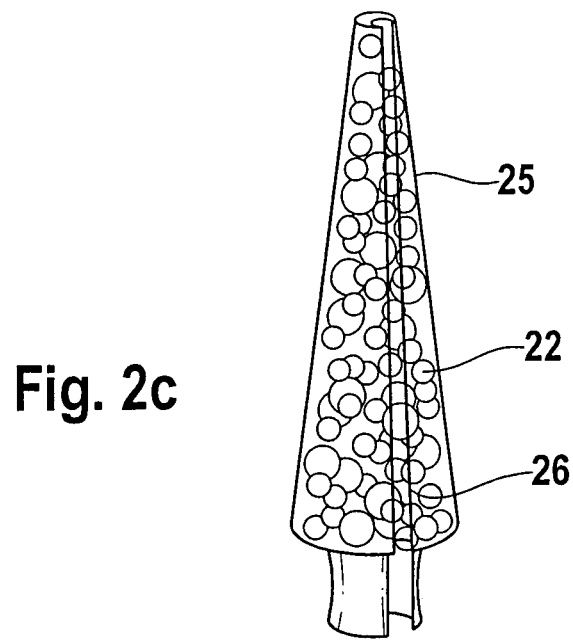
FIG. 2c shows an additional embodiment of a microneedle 25 of an array according to the exemplary embodiments and/or exemplary methods of the present invention.

FIG. 2c shows an additional embodiment of a microneedle 25 of an array according to the present invention, which has a channel 26 in the side wall, besides microporous structure 22. In this embodiment too, the introduction of active agent may take place via channel 26, while the microporous structure is predominantly used for degradability.

Figure 3A:
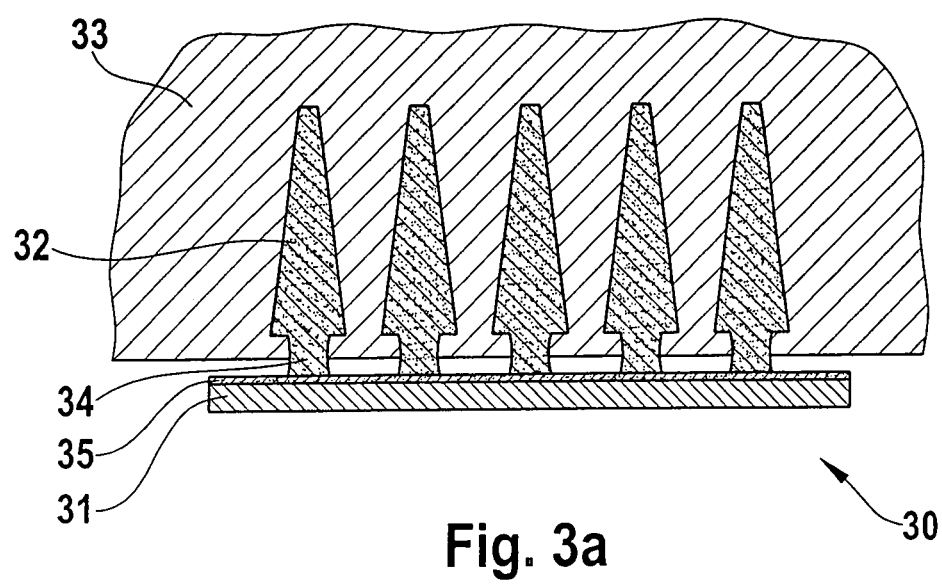
FIG. 3a shows an array 30 according to the exemplary embodiments and/or exemplary methods of the present invention.

FIG. 3a shows an array 30 according to the exemplary embodiments and/or exemplary methods of the present invention, having a carrier substrate 31 and microneedles 32 after being placed on or in skin 33 of a patient. In the area of the transition to planar carrier substrate 31, microneedles 32 have preset breaking points 34. Planar carrier substrate 31 has an upper layer 35 made of porous silicon.

Figure 3B:
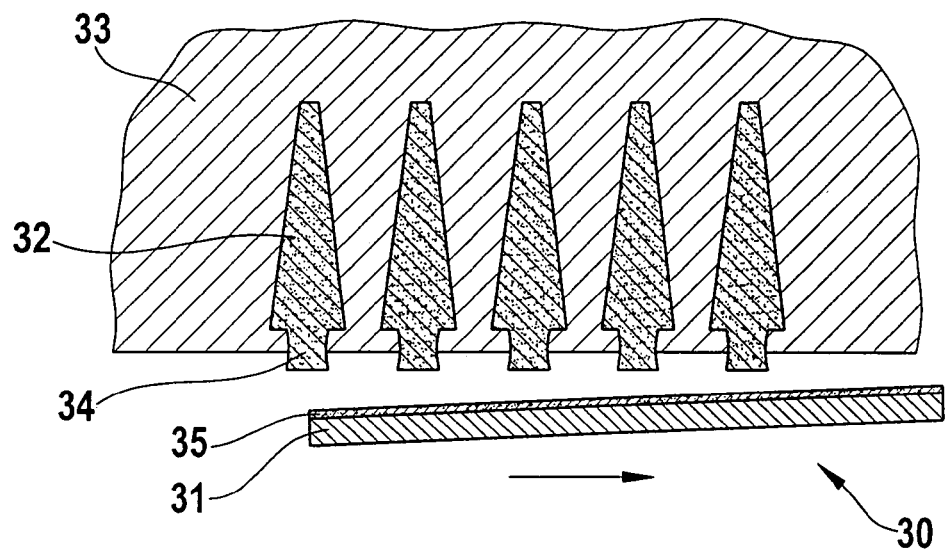
FIG. 3b shows the same array 30, after planar carrier substrate 31.

FIG. 3b shows the same array 30, after planar carrier substrate 31, after the placing of the array into skin 33, is disengaged from microneedles 32 by a lateral shearing motion indicated by the arrow, in that the microneedles are broken by the shearing motion in the area of preset breaking points 34, microneedles 32 remaining in skin 33. The introduction of the active agents can be managed either through active agents already held in reserve in the porous needle material or through active agent preparations applied from the outside.

Figure 4:
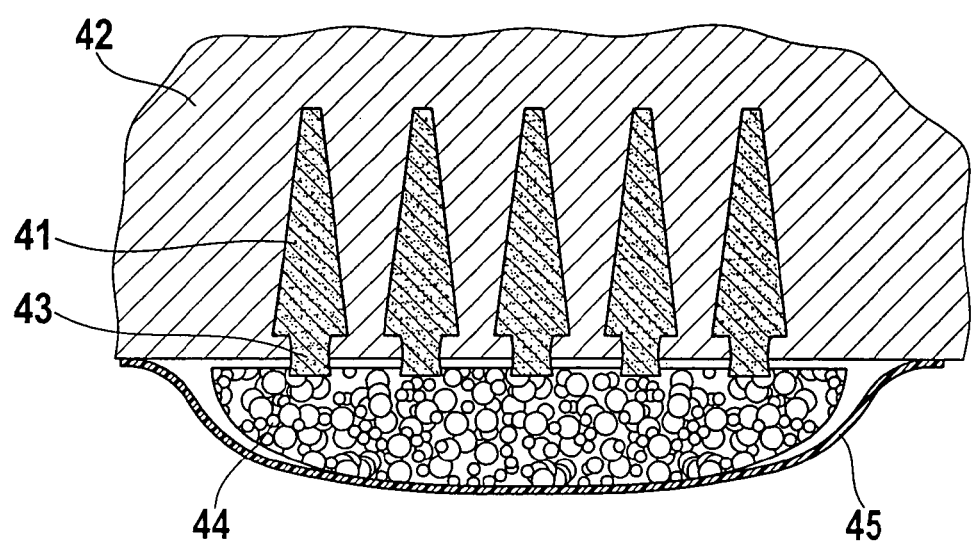
FIG. 4 shows microneedles 41 arranged in the manner described in skin 42 of a patient.

FIG. 4 shows microneedles 41 arranged in the manner described in skin 42 of a patient. The microneedles are particularly fixed in the area of preset breaking points 43, since the skin is elastic and has the tendency to contract around the taperings of preset breaking points 43 more strongly about microneedles 41.

As shown in FIG. 4, after placing the microneedles, an active agent plaster was placed on the skin, which is made up of storage of active agent 44 and of cover plaster 45. The cover plaster prevents the penetration of germs and pathogens. The active agents from the active agent storage diffuse either through the microporous structure of microneedles 41 or, in case these are provided, through centrical bores of the cannula-like microneedles, not shown in FIG. 4, through skin 42 and thus arrive in the blood circulation.

What is claimed is:
1. An array to be placed on the skin of a human patient or an animal patient for transdermally applying pharmaceuticals, toxins or active agents, comprising:
   a carrier substrate; and
   microneedles situated on the carrier substrate, the microneedles having a preset breaking point in an area of a transition to the carrier substrate, the preset breaking point including one of (a) a material tapering and (b) a constriction.

2. The array of claim 1, wherein the carrier substrate is planar.

3. The array of claim 1, wherein at least one of the microneedles and the carrier substrate are made up of a material containing silicon.

4. The array of claim 1, wherein the microneedles have one of a partially porous structure and a completely porous structure.

5. The array of claim 1, wherein the microneedles are in the form of cannulas.

6. The array of claim 1, wherein the planar carrier substrate is able to remain on the skin, after the array is placed on the skin.

7. The array of claim 1, wherein the needles have a structure on their surface that functions as a barbed hook.

8. The array of claim 1, wherein the microneedles are arranged in one of a rectangular array, a hexagonal array, and a random array.

9. The array of claim 1, wherein the array is one of square, rectangular, circular, and oval.

10. The array of claim 1, wherein the microneedles are made up of a biodegradable material.

11. The array of claim 1, wherein the microneedles hold in reserve the pharmaceuticals, toxins or active agents to be transdermally applied.

12. The array of claim 1, wherein the carrier substrate is a flexible carrier substrate.

13. The array of claim 1, wherein the microneedles include one of a surrounding thin film and a foil.

14. The array of claim 13, wherein the one of the surrounding thin film and the foil includes a thin polyurethane film.

15. The array of claim 1, wherein the microneedles include a channel in a sidewall.

16. An array kit, comprising:
   an array to be placed on the skin of a human patient or an animal patient for transdermally applying pharmaceuticals, toxins or active agents, including a carrier substrate, and microneedles situated on the carrier substrate, the microneedles having a preset breaking point in an area of a transition to the carrier substrate, the preset breaking point including one of (a) a material tapering and (b) a constriction; and
   a cover material to be placed over the array after the array is placed in the skin.

* * * * *